US010179953B2

(12) United States Patent
Majd et al.

(10) Patent No.: US 10,179,953 B2
(45) Date of Patent: Jan. 15, 2019

(54) HYDROGEL-MEDIATED ELECTROPOLYMERIZATION OF CONDUCTING POLYMERS

(71) Applicant: The Penn State Research Foundation, University Park, PA (US)

(72) Inventors: Sheereen Majd, Houston, TX (US); Mohammad Reza Abidian, University Park, PA (US); Soohyun Park, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 359 days.

(21) Appl. No.: 15/036,202

(22) PCT Filed: Jan. 13, 2015

(86) PCT No.: PCT/US2015/011174
§ 371 (c)(1),
(2) Date: May 12, 2016

(87) PCT Pub. No.: WO2015/108857
PCT Pub. Date: Jul. 23, 2015

(65) Prior Publication Data
US 2016/0289851 A1 Oct. 6, 2016

Related U.S. Application Data

(60) Provisional application No. 61/927,331, filed on Jan. 14, 2014.

(51) Int. Cl.
C25D 5/02 (2006.01)
C25D 5/06 (2006.01)
(Continued)

(52) U.S. Cl.
CPC ............. C25B 3/00 (2013.01); A61L 27/50 (2013.01); A61L 27/52 (2013.01); C08G 61/124 (2013.01);
(Continued)

(58) Field of Classification Search
CPC ............. C25D 9/02; C25D 5/06; C25D 5/02
(Continued)

(56) References Cited

U.S. PATENT DOCUMENTS

2013/0126220 A1* 5/2013 Nishizawa ........... A61N 1/0496
174/257

FOREIGN PATENT DOCUMENTS

CN 103255433 A 8/2013

OTHER PUBLICATIONS

Kim et al, "Conducting polymer grown in hydrogel scaffolds coated on neural prosthetic devices," Journal of Biomedical Materials Research Part A, vol. 71A, Issue 4, 2004, p. 577-585. (Year: 2004).*
(Continued)

Primary Examiner — Brian W Cohen
(74) Attorney, Agent, or Firm — McDermott Will & Emery LLP

(57) ABSTRACT

Selective electropolymerization of conducting polymers using a hydrogel stamp is disclosed. The ability of this simple method to generate patterned films of conducting polymers with multiple surface chemistries in a single-step process and to incorporate biomolecules in these films is further described.

15 Claims, 3 Drawing Sheets

(51) Int. Cl.
*C25D 9/02* (2006.01)
*C25B 3/00* (2006.01)
*A61L 27/50* (2006.01)
*A61L 27/52* (2006.01)
*C08G 61/12* (2006.01)

(52) U.S. Cl.
CPC ............. *C08G 61/126* (2013.01); *C25D 5/02* (2013.01); *C25D 5/06* (2013.01); *C25D 9/02* (2013.01); *C08G 2261/1424* (2013.01); *C08G 2261/3221* (2013.01); *C08G 2261/3223* (2013.01); *C08G 2261/44* (2013.01); *C08G 2261/512* (2013.01); *C08G 2261/514* (2013.01); *C08G 2261/794* (2013.01)

(58) Field of Classification Search
USPC .................................................. 205/117, 118
See application file for complete search history.

(56) References Cited

OTHER PUBLICATIONS

M. Stevens et al., "Direct patterning of mammalian cells onto porous tissue engineering substrates using agarose stamps," Biomaterials, 26, (2006) 7636-7641.

T. Kauffmann et al., "Stamps, inks and substrates: polymers in microcontact printing," Polym. Chem., 2010, 1, pp. 371-387, Jan. 11, 2010.

S. Majd et al., "Hydrogel Stamping of Arrays of Supported Lipid Bilayers with Various Lipid Compositions for the Screening of Drug-Membrane and Protein-Membrane Interactions," Angew. Chem. Int. Ed. 2005, 44, pp. 6697-6700, Sep. 27, 2005.

R. J. Waltman et al., "Electrically conducting polymers: a review of the electropolymerization reaction, of the effects of chemical structure on polymer film properties and of applications towards technology," Can. J. Chem. 64, pp. 76-96, 1986.

X. Cai et al.., "Fabrication of Ultrafine Soft-Matter Arrays by Selective Contact Thermochemical Reaction," Scientific reports 3, pp. 1-5, May 7, 2013.

International Search Report and Written Opinion issued in Application No. PCT/US2015/011174 dated Apr. 27, 2015.

\* cited by examiner

HYDROGEL-MEDIATED ELECTROPOLYMERIZATION OF CONDUCTING POLYMERS

CROSS-REFERENCE TO RELATED APPLICATION

This application is a U.S. National Phase under 35 U.S.C. § 371 of International Application No. PCT/US2015/011174, filed Jan. 13, 2015, which claims the benefit of U.S. Provisional Application No. 61/927,331, filed Jan. 14, 2014, the entire disclosures of which are hereby incorporated by reference herein.

TECHNICAL FIELD

The present disclosure is directed to forming conductive polymers by electrodeposition of the polymer from a hydrogel stamp loaded with polymer precursor materials. The present disclosure is particularly useful for preparing patterned conductive polymers by electrodeposition from a hydrogel stamp.

BACKGROUND

Conducting polymers (CPs) have been applied in a number of fields ranging from flexible electronics and sensing to energy storage. The growing interest in these materials stems from their unique and tunable physical and chemical properties. CPs have conjugated double-bonded backbone that provides electrical conductivity after doping. Electrochemical oxidation and reduction of these polymers can change their color, volume, conductivity, and wettability. Moreover, CPs can easily be decorated with functional molecules including bioactive proteins and drugs or can entrap these molecules for controlled release upon electrical stimulation. In the biomedical field, surfaces with patterned films of CP offer attractive platforms for studies of in vitro cell attachment and growth, tissue regeneration, neural electrodes, or biosensing. In this context, polypyrrole (PPy) and poly(3,4-ethylenedioxythiophene) (PEDOT) have become particularly popular due to their superior conductivity, chemical stability, and biocompatibility.

PPy and PEDOT polymers are commonly synthesized through chemical or electrochemical polymerization. In addition, CPs can be patterned either through selective removal of parts of an existing film or selective deposition of the polymer. To date, both approaches have been employed through variety of techniques such as inkjet printing, infrared laser, photolithography, e-beam lithography, dip-pen nanolithography, and microcontact printing. Among these techniques, microcontact printing offers a low-cost and versatile approach to pattern CP films, with resolutions acceptable for most biomedical applications, compared to other methods where sophisticated instruments are often required.

Microcontact printing is accessible to any ordinary laboratory since stamps are prepared from elastomeric materials, such as polydimethylsiloxane (PDMS), casted from a microfabricated mold. Within the past few years, hydrogels have been explored as an alternative for the traditional PDMS stamps in microcontact printing of hydrophilic substances. The porous and hydrated nature of hydrogels enables these stamps to absorb aqueous solutions of cells and biomolecules for subsequent patterning. These stamps have also been utilized in fabrication of micro and nano-scale structures on glass substrates.

Larsen and colleagues employed hydrogel stamps to deliver an etchant chemical for selective removal of parts of a preformed CP film, producing a patterned polymer film. T. S. Hansen, K. West, O. Hassager, N. B. Larsen, *Adv. Mater.* 2007, 19, 3261. In another study, these authors further extended the application of hydrogel stamps to generate patterned CP films with various chemistries in register. This subtractive approach, however, required several consecutive steps for generating the patterned CP film with multiple chemistries. Lind, et al., *Langmuir* 2012, 28, 6502. Accordingly a continuing need exists for preparing conductive polymers and preparing patterned conductive polymers.

SUMMARY OF THE DISCLOSURE

Advantages of the present invention include methods of forming a conductive polymer and forming patterns including one or more conductive polymers. The conductive and patterned conductive polymers can advantageously include a variety of materials, e.g., biomolecules, and the methods can generate such polymers with different dopants and/or different biomolecules simultaneously in a single-step process. The conductive and patterned conductive polymers can also advantageously be formed as a gradient and/or with a gradient of one or more materials.

An additional advantage of the present invention is a method of forming a conductive polymer comprising: contacting a conductive substrate with a hydrogel stamp containing (i) at least one monomer capable of forming the conductive polymer and (ii) at least one dopant; and applying a current between the conductive substrate and hydrogel stamp to form the conductive polymer on the conductive substrate. The method can advantageously employ a hydrogel stamp with a pattern and form the conductive polymer on the conductive substrate according to the pattern of the stamp. The hydrogel stamp can also include at least one biomolecule and/or a second set of monomers/dopants to generate conductive polymers with different monomers/dopants and/or different biomolecules simultaneously in a one step process.

Another aspect of the present disclosure includes a method of forming a pattern including one or more conducting polymers. The method comprises: contacting a hydrogel stamp loaded with one or more polymer precursor solutions with an electrically conducting surface of a substrate; and applying an electrical current between the hydrogel stamp and the electrically conducting surface of the substrate to form a pattern including one or more conducting polymers on the substrate.

Embodiments of the present disclosure include one or more of the following features individually or combined. For example, the hydrogel stamp can be loaded with at least two different polymer precursor solutions. The formed pattern can include at least two different conducting polymers on the substrate which is formed in the single step of applying the electrical current between the hydrogel stamp and the electrically conducting surface of the substrate. In some embodiments, the hydrogel stamp is loaded with one or more materials, e.g., one or more biomolecules. In other embodiments, the pattern includes one or more conducting polymers having a feature size between 40 microns and 1,000 microns. In still further embodiments, the hydrogel stamp can be loaded with a gradient of polymer precursor solution and/or a gradient of a material, e.g., a biomolecule. Such a loading can be carried out by an asymmetric inking of a hydrogel stamp, for example. The pattern formed from such a loaded hydrogel stamp could include the one or more conductive polymers having at least one gradient conductive polymer and/or at least one gradient material.

In still other embodiments, the method can advantageously comprise forming at least 10 additional patterns including the one or more conducting polymers using the hydrogel stamp without reloading the hydrogel stamp with polymer precursor solution. In additional embodiments, the method can advantageously comprise transferring the pattern from the substrate to a second substrate, e.g., onto an insulating surface of the second substrate and/or onto a flexible substrate.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIG. 1A shows a schematic illustration of patterning of conducting polymer films on a gold-coated substrate using an agarose stamp that is loaded with the polymer precursor solution. RE, CE and WE in FIG. 1A represent reference, counter, and working electrodes respectively. FIG. 1B shows an optical image of a representative patterned PPy film produced by this technique. The features, i.e., circular posts, had diameters ranging from 40 microns to 1 mm (FIG. 2A).

FIG. 2A shows circular features prepared from a stamp with circular posts while the features in FIGS. 2B and 2C were prepared with a stamp with linear posts of 100 μm width with two different configurations.

FIG. 2D shows the change in the size of deposited PPy film spots as a function of the hydrogel post diameter (circular features). Error bars represent standard error of the mean (N≥60), and the dashed line represents the best linear fit to the data ($R^2$=0.9797). FIG. 2E shows the thickness of the deposited PPy film as a function of the electrodeposition time. Error bars in this graph represent standard error of the mean, and the dashed line shows the best linear fit to the data ($R^2$=0.9668). FIG. 2F is a comparison of the impedance (log values) of the bare electrode and PPy patterned electrode. The error bars show standard error of the mean (P<0.05, N=3).

FIG. 3C is ATR-FTIR spectroscopy of PPy film with and without entrapped biotin. FIG. 3D is ATR-FTIR spectroscopy of PPy spots doped with polystyrene sulfonate (PSS) and dodecylbenzenesulfonate (DBS) on the same substrate, as illustrated in the cartoon inset in this panel where different spots of the patterned PPy were doped with: PSS (black), DBS (light gray), or $ClO_4$ (medium gray). FIG. 3E is an energy dispersive spectroscopy (EDS) of PPy film spots doped with PSS and $ClO_4$, on the same substrate examined in panel (FIG. 3D).

DETAILED DESCRIPTION OF THE DISCLOSURE

Figures 1A, 1B:
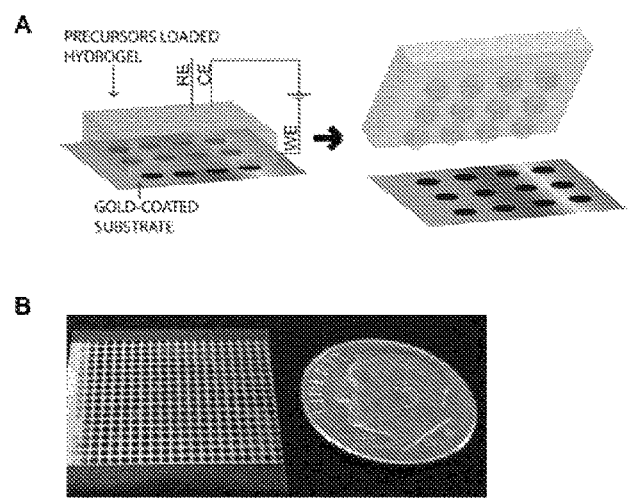
FIGS. 1A and 1B show hydrogel-mediated electrodeposition of conducting polymer films according to embodiments of the present disclosure.

The present disclosure relates to methods of forming and patterning conductive polymers. Methods of the present disclosure include contacting a conductive substrate with a hydrogel stamp and applying a current between the conductive substrate and hydrogel stamp to form the conductive polymer on the conductive substrate. The hydrogel stamp can be loaded (also referred to herein as inking) with one or more polymer precursor solutions. The precursor solutions contain (i) at least one monomer capable of forming the conductive polymer and (ii) at least one dopant. The precursor solutions can also contain other materials, e.g., at least one biomolecule. The hydrogel stamp can be loaded with the one or more polymer precursor solutions by applying the one or more polymer precursor solutions to the stamp. The stamp can also be loaded with the one or more polymer precursor solutions by applying one or more monomers and one or more dopants to the stamp as separate components rather than as a solution. Additional materials, biomolecules, can be added to the stamp as separate components as well.

The methods of the present disclosure advantageously allow applying hydrogel stamps for patterning conductive polymer (CP) films with multiple chemistries in a single-step process. For example, the hydrogel stamp can include different monomer/dopant combinations at different locations of the stamp and/or the stamp can include materials at different locations and/or different materials at different locations of the stamp. For example, the hydrogel stamp can also include a second set of (iii) at least one monomer capable of forming the conductive polymer and (iv) at least one dopant at a different location of the hydrogel stamp and which is different than the first set of monomer/dopant combination. When applying the current between the conductive substrate and hydrogel stamp, the conductive polymer on the conductive substrate is formed with different materials resulting from the first and second set of monomer/dopant combinations.

Another aspect of the present disclosure includes methods of forming a pattern including one or more conducting polymers. The method includes: contacting a hydrogel stamp loaded with one or more polymer precursor solutions with an electrically conducting surface of a substrate; and applying an electrical current between the hydrogel stamp and the electrically conducting surface of the substrate to form a pattern including one or more conducting polymers on the substrate. Advantageously, the hydrogel stamp can be loaded (inked) with different combinations of monomers/dopants and/or materials. The pattern formed from such a loaded hydrogel stamp would include different conductive polymers corresponding to the different combinations of monomers/dopants and/or materials and would be formed in the single step of applying the electrical current between the hydrogel stamp and the electrically conducting surface of the substrate.

The hydrogel stamp can also advantageously be loaded with a gradient of polymer precursor solution and/or a gradient of a material, e.g., a biomolecule. The pattern formed from such a loaded hydrogel stamp would include the one or more conductive polymers having at least one gradient conductive polymer and/or at least one gradient material.

Additional advantageous of the methods of the present disclosure include transferring the pattern from the substrate to a second substrate. The second substrate can be an insulator or have an insulating surface onto which the pattern is transferred. In addition, or alternatively, the second substrate can be flexible, thus allowing the formation of a conductive polymer pattern on a flexible, insulating substrate.

In practicing embodiments of the method, the surface of a metal (e.g., copper, silver, gold) coated substrate can be used as the electrically conducting surface of the substrate. Additionally, the pattern can include one or more conducting polymers having a feature size between 40 microns and 1,000 microns (1 mm).

Monomers and dopants that are useful in practicing the present disclosure include pyrrol, 3,4-ethylenedioxythiophene, anilin, tiophene, acetylene, o-methoxyaniline among other conjugated monomers and polystyrenesulfonate, dodecylbenzenesulfonate, perchlorate, p-toluenesulfonic acid, tetrafluoroborate, hyaluronic acid among a number of other negatively-charged proteins and drugs that can be used as dopants. In fact any monomer or dopant that generates a conductive polymer can be used in practicing embodiments of the present disclosure.

Materials that are useful in practicing the present disclosure include, biomolecules such as growth factors, proteins, peptides, drugs, and chemical reagents.

In practicing preferred embodiments of the present disclosure, referred to as hydrogel-mediated electropolymerization, a wet hydrogel stamp provides a polymer precursor solution (i.e. at least one monomer and at least one dopant) to an electrode surface and upon application of a current, a CP film with controlled thickness forms only in the areas of contact between the hydrogel and electrode. A hydrogel stamp offers the advantage over polymerizing the conductive polymer from solution in that the stamp can be in a shape that allows patterning of the formed polymer films.

FIG. 1A illustrates, for example, a hydrogel-mediated electrodeposition of a pattern of conducting polymer films by contacting an agarose stamp that is loaded with a polymer precursor solution with a gold-coated substrate. The hydrogel stamp has features, e.g., posts, which only contact the conductive substrate and by applying a current between the conductive substrate and hydrogel stamp, a pattern of conductive polymer films in the shape of dots form on the conductive substrate. This solution-free technique also affords simultaneous deposition of different CP/dopant compositions on a substrate in parallel within a single deposition step. In addition, the biocompatible and wet hydrogel stamp provides an ideal environment for storage and delivery of bioactive molecules to the site of polymerization, enabling easy entrapment of these biomolecules in the produced film of CP.

To generate patterned films of PPy, we placed an agarose stamp, inked with the monomer/dopant (pyrrole (Py)/polystyrene sulfonate (PSS)) solution, into contact with a conductive substrate (in this case, gold-coated plastic cover slip). We then applied a current between the gold substrate and the stamp, using a three-electrode setup, which resulted in the electropolymerization of Py at the sites of contact between the stamp and gold substrate (FIG. 1A).

Figures 2A, 2B, 2C, 2D, 2E, 2F:
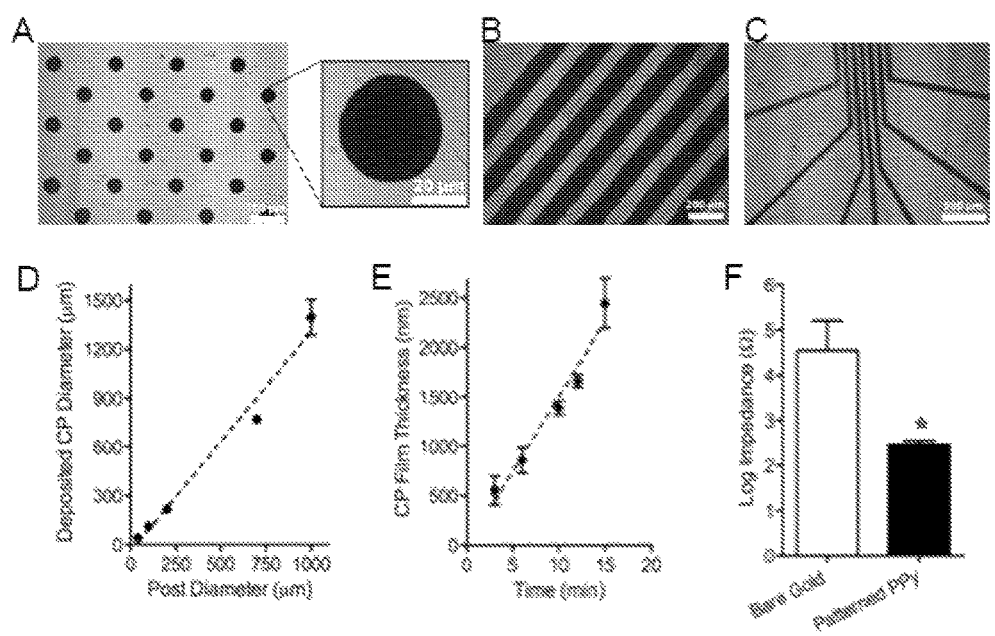
FIGS. 2A, 2B and 2C shows optical images of patterned PPy films produced according to an embodiment of the present disclosure from a hydrogel stamp.
FIGS. 2D, 2E and 2F are charts characterizing some aspect of patterns including one or more conducting polymers formed according to embodiments of the present disclosure.

Under these conditions, the hydrogel acts as a carrier of the polymer precursors and thus, restricts the polymer electrodeposition to selected areas of the gold substrate. FIG. 1B illustrates a representative substrate patterned with PPy films using this technique. To assess the flexibility of this method to generate different patterns of CP, we employed agarose stamps with circular posts of diameters ranging from 40 μm to 1 mm and stamps with linear posts of 100 μm width to pattern PPy films. Application of these stamps for electropolymerization produced positively-patterned PPy films with high-fidelity, as illustrated in FIG. 2A and 2D. The graph in FIG. 2D shows an excellent linear correlation ($R^2$=0.9797) between the agarose stamp post size and the diameter of the deposited PPy spots. These results demonstrate the versatility of the present technique to generate patterns of CP films with various sizes and shapes.

To better characterize the resultant CP films, we examined their thickness and electrical property. For thickness measurements, we applied agarose stamps loaded with 0.1 M Py/0.1 M PSS for electrodeposition with time durations of 3-15 min and characterized the deposited PPy films on gold substrates using field emission scanning electron microscopy (FESEM). FESEM images revealed that the polymer thickness increased linearly with an increase in electrodeposition time, as depicted in FIG. 2E. This data shows that electropolymerization through hydrogel stamp allows controlling of the deposited CP film thickness, similar to the solution-based electrodeposition.

For electrical property measurements, we evaluated the impedance of the gold electrodes at 1 kHz before and after deposition of patterned PPy film. As FIG. 2F shows, the patterned PPy film reduced the impedance of the gold substrates by approximately 99.4%, confirming the conductivity of the produced PPy films on gold. These results are in good agreement with the previous reports on surface modification of neural electrodes with CPs (including PPy) to lower the impedance of these electrodes for improved neural recordings. See, e.g., M. R. Abidian, D. C. Martin, *Adv. Funct. Mater.* 2009, 19, 573.

The absorbent nature of hydrogels makes them capable of storing materials and solutions for multiple deliveries. Indeed, agarose stamps loaded with biomolecules have been previously applied for patterning 30-100 arrays of biomolecules without intermediate inking See S. Majd, M. Mayer, *Angew. Chem., Int. Ed.* 2005, 44, 6697.

Based on this capability, a hydrogel stamp loaded with monomer and dopant would be able to deliver these materials to several substrates, one after another, for selective deposition of polymer films on these electrodes. This was shown by an agarose stamp with 0.3 M Py/0.3 M PSS which was applied for consecutive electrodeposition of PPy on 10 gold substrates. This stamp successfully deposited PPy on all the gold substrates without any detectable difference in the quality of polymer film. The hydrogel-mediated electropolymerization technique presented here can, hence, be applied for large-scale production of patterned CP films in a rapid and efficient manner. In an embodiment of the present disclosure, the method of forming a pattern including one or more conducting polymers can include forming at least 10 additional patterns using the hydrogel stamp without reloading the hydrogel stamp with polymer precursor solution.

Patterned CPs are particularly attractive when they present multiple chemistries in a spatially addressable fashion. That is, patterns that include conductive polymers made from different monomer/dopant and/or monomer/dopant/material combinations at different locations within the pattern are particularly attractive. These patterns, for instance, provide an appealing platform for analyzing interactions of cells with surfaces of various chemistries, which can simply be achieved through incorporation of different dopants or bioactive molecules in the CP film.

Figures 3A, 3B, 3C, 3D, 3E:
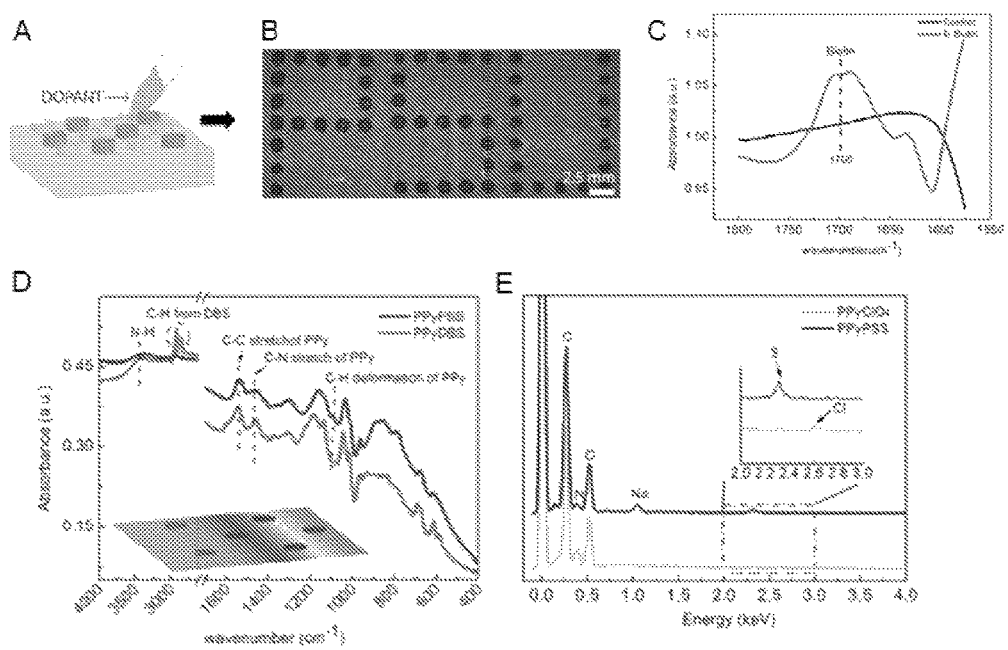
FIG. 3A is a cartoon illustration and FIG. 3B is optical image of selective loading of posts on a hydrogel stamp.
FIGS. 3C, 3D and 3E are charts characterizing some aspect of patterns including one or more conducting polymers formed according to embodiments of the present disclosure.

To examine the capability of the present technique to generate patterned CPs with multiple chemistries, we first tested if we can control the CP polymerization on a substrate spot by spot by selective inking of the posts on a stamp. To this end, we used a 2% (w/v) agarose stamp that was previously loaded with 0.5 M of Py (by immersing the entire stamp in the monomer solution) and individually inked alternating posts on the stamp with a 0.5 M PSS dopant solution, leaving other posts with no dopant. See FIG. 3A which illustrates applying dopant to select posts on the stamp. Electropolymerizing the polymer precursor from this stamp led to the deposition of PPy only on the spots where the corresponding posts were inked with the dopant solution (FIG. 3B). No polymer growth was observed in the rest of the substrate despite the presence of high concentration of Py throughout the stamp.

These results confirm that we can address different spots in a patterned CP film, produced by this method, individually. Employing the same technique, we fabricated a patterned PPy film with multiple chemistries by selective inking of posts of a 0.5 M Py-loaded stamp with one of three different dopant solutions: 0.5 M PSS, 0.25 M dodecylbenzenesulfonate (DBS), and 0.5 M perchlorate ($ClO_4$). The presence of these dopants in different spots was confirmed either by attenuated total reflectance-Fourier transform infrared spectroscopy (ATR-FTIR) or by energy dispersive spectroscopy (EDS).

Using ATR-FTIR, we were able to detect the presence of DBS and PSS in the PPy film, while $ClO_4$ was not easily detectable (FIG. 3D). We therefore, applied EDS as a complimentary detection method by which we were able to confirm the presence of PSS and $ClO_4$ in PPy patterned spots (FIG. 3D). In FIG. 3C, the vibration bands at 3433 $cm^{-1}$ correspond to the N—H stretching of PPy and the absorption at 1540 $cm^{-1}$ represents the C—C and C=C stretching in the PPy ring and can hence, be regarded as characteristic absorption of PPy. The absorption range of 2800-2990 $cm^{-1}$ corresponds to the long alkyl chain of DBS. From the EDS data in FIG. 3E, Cl from $ClO_4$ and S from PSS were clearly detected. These findings demonstrate that a single hydrogel stamp can be applied to deliver multiple distinct dopants and to produce patterned CP films with various chemistries and properties on the same substrate in a single-step procedure.

Decoration of CPs with bioactive molecules such as proteins is essential for most biomedical applications of these polymers. It has been previously demonstrated that such molecules can easily be entrapped within the CP network during electropolymerization process. To assess the applicability of the hydrogel-mediated electrodeposition for the fabrication of CP films including biomolecules, we included D-biotin molecules in the inking solution used for the hydrogel stamp and tested the resultant PPy films for the presence of biotin following a procedure previously reported by George et al. (*Adv. Mater.* 2006, 18, 577).

In this case, DBS was used as a dopant (at very low concentration in order to favor the inclusion of D-biotin). Briefly, a polymer precursor solution of 0.1 M Py, 0.01 M DBS, and 0.04 M D-biotin was prepared and used to ink an agarose stamp. The stamp was subsequently contacted with an electrically conductive surface of a substrate and a current applied to electrodeposit a patterned PPy film onto the substrate. We confirmed the presence of D-biotin in the resulting PPy films by fluorescence imaging and ATR-FTIR. When exposed to the fluorescent-labeled streptavidin (a protein that binds to biotin with high affinity), biotin-containing PPy films showed significantly higher fluorescence intensity compared to the control PPy films with no biotin.

Moreover, ATR-FTIR spectroscopy of the biotin-containing PPy films confirmed the presence of biotin in these films, where an absorbance peak at 1700 $cm^{-1}$ wavelength represented the carbonyl bond in D-biotin structure, as illustrated in FIG. 3B. As expected, this peak was not detectable in the control PPy films. This study confirmed the incorporation of bioactive molecules in the CP films electrodeposited through hydrogel stamps. This capability makes the present technique attractive for fabrication of patterned films of CP decorated with biomolecules, or potentially, several different biomolecules in an addressable fashion, for studies of cell adhesion and growth.

In order to test the capability of the developed technique to electropolymerize other conducting polymers (CPs), we employed 3,4-ethylenedioxythiophene (EDOT) as a monomer and polystyrene sulfonate (PSS) as a dopant. Poly(3,4-ethylenedioxythiophene) (PEDOT) is another CP with great biocompatibility and chemical stability as PPy, and thus readily utilized in biomedical applications. Since EDOT has low solubility in a hydrophilic solution, 0.1 M EDOT was prepared in 1:1 v/v $dH_2O$:Acetonitrile solution. A 2% agarose hydrogel was inked with 0.1 M EDOT and 0.1 M PSS solution for 20 minutes and applied for the hydrogel-mediated electropolymerization. Patterned PEDOT films with circular features with diameters of 700 µm and 200 µm were achieved and demonstrating successful deposition of PEDOT films. These PEDOT films had an average impedance of 43.68±3.04Ω. Multiple deposition of the patterned substrates without re-inking the precursor solution was also possible with PEDOT:PSS. Patterned PEDOT:PSS films with 200 µm circular features were achieve with at least six repeated electrodepositions from a single-loaded agarose hydrogel.

We also extended this technique to create CP substrates with chemical and biomolecular gradients. Fixed gradients of biomolecules and/or chemicals, such as growth factors and proteins, can be utilized to control cellular behaviors and hence, is a critical factor for engineering cells and tissues. While techniques including microfluidics and click-chemistry have been used to create gradients on CP films, our technique offers a simple and flexible procedure to generate a gradient of CP and gradients of biomolecules.

First, a gradient of CP was achieved by asymmetric inking of an agarose hydrogel stamp with linear features with width of 1.5 mm and length of 1.5 cm. In particular, 0.5 M Py was distributed equally in the hydrogel. Then on one side (cross-section of the linear features), the hydrogel was immersed in 0.5 M PSS solution allowing diffusion derived inking of dopant along the linear feature of the hydrogel. The duration of inking was varied (5-30 min) in order to assess the effect of time-dependent diffusion of dopant on CP deposition. The subsequent electrodeposition of the asymmetrically inked hydrogel resulted in formation of CP gradient on the substrate.

Optical images of the PPy:PPS films indicate that there may be a difference in the thickness of deposited films along the line. Further, we observed time-dependent extension of CP films. Lengthier CP deposition after 20 min inking compared to 5 min demonstrates the further diffusion of PSS solution made with longer inking The impedance measurements on these gradients of CP films, however, did not show significant differences with longer inking, presumably due to the large surface area subjected for the measurements.

As we demonstrated that the gradient inking of a dopant in the hydrogel could create gradient film of CP, we extended this technique to create 2-way gradients of two different dopants: PSS and laminin peptide. This laminin peptide used here was modified to present cell binding motif and to carry negative charge at neutral pH so that it can be used as dopant; peptide sequence was NH2-DEDEDY-FQRYLI-COOH. A solution of 0.5 M Py was first distributed in the agarose hydrogel with the linear features described previously. Then, each end of the linear feature was inked with a dopant; left-end was inked with 0.5 M PSS, and right-end was inked with 5 mg/ml of the laminin peptide. 1-D diffusion of two dopants from the two opposite ends of the linear feature of the stamp was induced for 30 min, and the inked hydrogel was then used for the electropolymerization.

Figure 4:
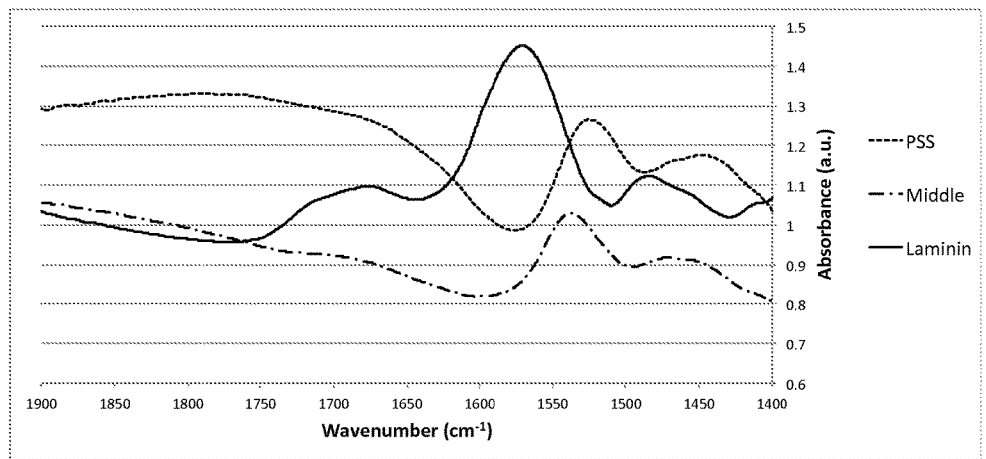
FIG. 4 shows FTIR spectra of PPy films with 2-way gradients of PSS and laminin peptide.

The deposited film of PPy had no difference in appearance throughout the feature. In order to confirm that we formed gradients of two different dopants, we sampled FTIR spectra from three different regions of the deposited PPy film along the line. As FIG. 4 demonstrates, we were able to detect the presence of corresponding dopants from each end of the film. For instance, the carbonyl bond peak around 1700 cm$^{-1}$ was only detected from the laminin-inked end of the film, but not in the middle or PSS-inked end. This indicates that the laminin had not diffused to the middle of the hydrogel during the 30 min inking time while PSS diffused to the middle of the gel.

Figure 5:
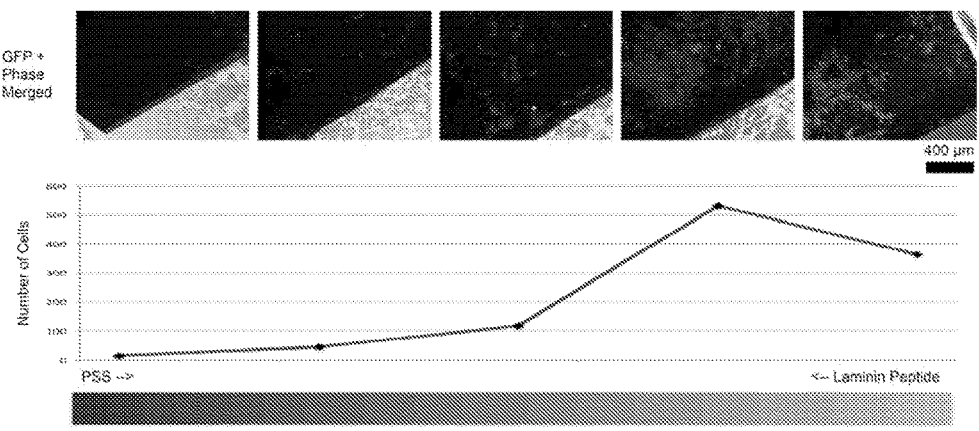
FIG. 5 is a chart showing optical images (combined fluorescent and phase-contrast images) of representative parts of the linear PPy films with the 2-way gradients of PSS and laminin peptide and adhered U87 glioblastoma cells. The number of cells (labeled green) on each part of the line was quantified via Live/Dead assay, and the schematic illustration of the 2-way gradients is indicated on the bottom. Preferential adherence of the cells onto laminin-doped portion of the film was apparent.

This 2-way gradient film was then subjected for the cell viability test. We previously confirmed that the PPy:PSS films showed restricted adhesion and proliferation of human primary glioblastoma (U87) cells while PPy:laminin presented normal level of cell binding and growth (data not shown). Thus, we expected to see biased cell attachment on the PPy film with PSS-laminin gradient. As FIG. 5 shows, the U87 cells indeed preferentially adhered and grew on the laminin-inked ends of PPy film compared to the other end where doped with PSS. FIG. 5 demonstrates optical images of the U87 cells along the gradient line and the number of cells on the substrate changing along the axis of the film. The cell viability, tested via Live/Dead assay, demonstrated that the number of cells on the PSS-inked ends of the film was much lower than that of the other end. Through this experiment, we demonstrated not only we can produce 2-way gradients using the hydrogel-mediated electrodeposition, but also we can control the adhesion of cells on the patterned film. More complex gradients on CP films can be prepared by the present methods.

While the current technique deposits films of CP on a working electrode (i.e. a metal coated substrate such as a gold or indium tin oxide coated substrate), the deposition of CP films on a non-conductive (insulator) and soft substrate is highly desirable for its application in flexible electronics. Here, we tested the capability of the current technique to transfer deposited patterned CP films onto polydimethylsiloxane (PDMS).

In this regard, we cured a thin film of PDMS (<1 mm) on top of the substrate with patterned PPy:PSS films. The cross-linking of PDMS was performed at room temperature for 48 hours in order to avoid heating the plastic cover slip. After curing, the PDMS was gently peeled off from the gold substrate, and only patterned CP films were transferred onto the PDMS. This CP patterned PDMS substrate now showed a flat surface as PDMS leveled the thickness of the CP films during cross-linking The thin PDMS substrates showed high flexibility and transparency. The PDMS substrate could be rolled as a piece of paper. Further, as PDMS is non-conductive, only patterned CP films can carry electrical charges on this substrate. More complicated electrical circuits can be achieved according to methods of the present disclosure for applications in flexible electronics.

Lastly, we modified the electropolymerization procedure to deposit CP films on the agarose hydrogel instead of deposition on the working electrode. Coating the hydrogel surface with CP films may provide a surface for cellular studies as hydrogels offer hydrophilic environment for fragile biomolecules and additional inking of hydrogel with other biomolecules may deliver the biomolecule to the network of CP films as well. The deposition of CP films on the hydrogel was achieved by sequential applications of high current during the electrodeposition.

For instance, the hydrogel with linear features were inked with 0.5 M Py and 0.5 M PSS solutions. The precursor loaded hydrogel was placed on the working electrode, and the current density of 1 mA/cm$^2$ was applied twice for 5 minute each. While the single application of current resulted in the deposition of CP films on the working electrode only, the second application of the current not only resulted in thicker CP films but also caused the growth of CP films on the hydrogel. The PPy:PSS films on hydrogel showed good transparency.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Materials: High gel strength agarose was obtained from OmniPur (Merck, Darmstadt, Germany). Py, EDOT, NaPSS, NaDBS, LiClO$_4$, and D-biotin were purchased from Sigma-Aldrich CO. LLC (St. Louis, Mo.). Bovine serum albumin (BSA) was from Amresco LLC (Solon, Ohio), and Texas Red-conjugated streptavidin was from Molecular Probes, (Eugene, Oreg.). Laminin peptide was prepared at the Macromolecular core facility at Penn State University (Hershey, Pa.).

Substrate Preparation: Plastic coverslips coated with gold, used as conductive substrates, were prepared by an evaporation method using Semicore E-gun/Thermal Evaporator at Penn State Nanofabrication Laboratory. In brief, plastic coverslips (22 mm$^2$, VWR International, Radnor, Pa.) pre-cleaned with isopropanol and distilled water, were coated with an 8 nm thick titanium layer as an adhesive layer followed by a 30 nm thick gold (Au) layer.

Fabrication and Inking of Stamp: Agarose stamps were prepared by casting the gel on PDMS molds with desired negative features as previously described. See S. Majd, M.

Mayer, *Angew. Chem., Int. Ed.* 2005, 44, 6697; S. Majd, M. Mayer, *J. Am. Chem. Soc.* 2008, 130, 16060. The agarose content in the hydrogel was varied from 2 to 4% (w/v); we applied higher agarose content for the stamps with smaller features (≤100 μm) to enhance the mechanical robustness of the posts. For most experiments, the hydrogel stamp was inked by immersion in a polymer precursor solution of monomer/dopant (with concentrations specified in the text) for about 20 min, and the excess fluid on the gel surface was air-dried for about 20 min at room temperature prior to electrodeposition.

Electrodeposition: Electrodeposition was performed by an Autolab electrochemical workstation (Metrohm Autolab B.V., Utrecht, Netherlands). The working electrode was connected to the gold substrate, and the inked stamp was placed onto the substrate (with posts facing down) using a rolling motion to avoid entrapment of air bubbles. Then, the reference and counter electrodes were brought into contact with the hydrogel top surface. The electrodeposition protocol was set by a software Nova 1.8 (Metrohm Autolab B.V.) to apply a constant current, which was calculated based on the current density of 0.5 mA/cm$^2$ and the surface area in contact with the gold substrate. The electrodeposition time was varied for different post diameters from 1 to 10 min; we typically applied longer deposition time for the stamps with larger features (e.g., ≥2 min for ≥700 μm features). After the polymerization, the hydrogel was carefully removed from the gold substrate leaving the patterned CP behind. It should be noted that in the presence of high monomer/dopant concentrations (≥0.5 M) in the stamp, longer deposition times (≥5 min) occasionally led to the difficulty in removal of the stamp from the electrode surface, presumably due to the growth of PPy into the gel network.

Entrapment of Biotin in CP film: For detection of D-biotin in PPy network by streptavidin binding, we first blocked the exposed substrate with 0.1% of BSA for 30 min at room temperature and then incubated the substrate in a solution of 0.1 mg/mL of Texas Redstreptavidin for 1 hour in dark. After washing the excess streptavidin from the substrate, the level of bound streptavidin to PPy films, with and without biotin, was evaluated under an inverted epi-fluorescence microscopy (Zeiss Axio Observer Z1, Carl Zeiss Microscopy).

CP films with gradients: PPy film with the 1-way gradient of PSS was prepared by asymmetrical inking of the hydrogel with linear topographical features. In the 2% agarose gel with Py distributed equally, the dopant, PSS, was inked only from one end of the linear feature. Inking time varied for 1-20 min to observe time-dependent diffusion of dopant in the hydrogel. Likewise, PPy film with the 2-way gradient of PSS and laminin peptide was prepared by inking the two dopants at each end of the linear feature on the hydrogel separately. For 2-way gradients, the hydrogel inked with the dopants for 20 minutes to ensure continuous formation of PPy along the linear feature.

CP Film Characterization: Upon electrodeposition, the patterned CP films were imaged under optical microscope (Zeiss Imager Z1, Oberkochen, Germany) at various magnifications. FESEM imaging of these films was performed using Nova NanoSEM 630 from FEI (Hilsboro, Oreg.) at Penn State Material Characterization Laboratory. The thickness measurements were obtained from the Nova NanoSEM software, xT Microscope Control.

Impedance measurements on the substrates were carried out using a three-electrode electrochemical set up from the Autolab potentiostat as previously described:[27] Briefly, the Ag/AgCl reference electrode was immersed into a 1× PBS (phosphate buffer saline) solution, while the working electrode was connected to the substrate and the counter electrode was connected to the electrolyte solution-containing cell. Impedance of the substrates with patterned PPy was measured at a physiologically relevant frequency of 1 KHz and compared to the bare substrate with no PPy film.

ATR-FTIR spectroscopy of the deposited PPy films was performed using Bruker Vertex 70 (Bruker Corporation, Billerica, Mass.) at Penn State Material Characterization Laboratory. The samples were scanned 100 times in the wavenumber range of 4000 to 400 cm$^{-1}$. The spectrum was plotted using the software for Bruker's infrared instruments, Opus version 7.0. EDS measurements were carried out using an FESEM with a silicon drift detector (area 80 mm$^2$, Oxford Instruments, UK) and the data was analyzed using Aztec Software.

In summary, we present a new approach to generate patterned CP films via electropolymerization through hydrogels. Unlike the common electrodeposition where an electrode is submerged in the solution of monomer and dopants, this approach relies on a topographically-patterned hydrogel to deliver the monomer/dopant solutions to selected areas of an electrode surface. We showed that this simple and solution-free electropolymerization technique could produce high-fidelity patterns of CPs with various geometrical shapes. In addition, a hydrogel stamp loaded with polymer precursors can deliver this material to multiple (≥10) substrates, one after another without re-loading, for rapid and efficient fabrication of a large number of patterned CP films. Furthermore, we demonstrated that by loading the hydrogel stamps with bioactive molecules, in addition to the polymer precursors, this technique produces patterned CP films with entrapped bioactive molecules, which are appealing platforms for cell studies. An attractive aspect of this approach is that a single hydrogel stamp can be applied to deliver multiple dopants in parallel and thus, to generate patterned CP films with multiple surface chemistries in a rapid single-step process. Therefore, this simple and readily-accessible method cab be applicable in a number of fields including cell and tissue engineering, biomaterials, biosensing, and bioelectronics.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A method of forming a conductive polymer, the method comprising: contacting a conductive substrate with a hydrogel stamp containing (i) at least one monomer capable of forming the conductive polymer and (ii) at least one dopant; and applying a current between the conductive substrate and hydrogel stamp to form the conductive polymer on the conductive substrate.

2. The method of claim 1, wherein the hydrogel stamp has a pattern and the formed conductive polymer is formed on the conductive substrate according to the pattern of the stamp.

3. The method of claim 1, wherein the hydrogel stamp further contains at least one biomolecule and the formed conductive polymer includes the at least one biomolecule.

4. The method of claim 1, wherein the hydrogel stamp contains a second set of (iii) at least one monomer capable of forming the conductive polymer and (iv) at least one dopant at a different location of the hydrogel stamp and which is different than the (i) at least one monomer capable of forming the conductive polymer and (ii) at least one dopant, and wherein applying the current between the conductive substrate and hydrogel stamp forms the conductive polymer on the conductive substrate wherein the conductive polymer is formed with different materials resulting from the second set of the (iii) at least one monomer capable of forming the conductive polymer and (iv) at least one dopant.

5. A method of forming a pattern including one or more conducting polymers, the method comprising:
contacting a hydrogel stamp loaded with one or more polymer precursor solutions with an electrically conducting surface of a substrate; and
applying an electrical current between the hydrogel stamp and the electrically conducting surface of the substrate to form a pattern including one or more conducting polymers on the substrate.

6. The method of claim 5, wherein the hydrogel stamp is loaded with at least two different polymer precursor solutions and the pattern includes at least two different conducting polymers on the substrate which is formed in the single step of applying the electrical current between the hydrogel stamp and the electrically conducting surface of the substrate.

7. The method of claim 5, wherein the hydrogel stamp is loaded with one or more materials.

8. The method of claim 5, wherein the stamp is loaded with one or more biomolecules.

9. The method of claim 5, wherein the pattern includes one or more conducting polymers having a feature size between 40 microns and 1,000 microns.

10. The method of claim 5, wherein the substrate is a metal coated substrate.

11. The method of claim 5, comprising forming at least 10 additional patterns including the one or more conducting polymers using the hydrogel stamp without reloading the hydrogel stamp with polymer precursor solution.

12. The method of claim 5, comprising loading the stamp with a gradient of polymer precursor solution and/or a gradient of a material and forming a pattern including the one or more conductive polymers having at least one gradient conductive polymer and/or at least one gradient material.

13. The method of claim 5, comprising transferring the pattern from the substrate to a second substrate.

14. The method of claim 13, wherein the pattern is transferred onto an insulating surface of the second substrate.

15. The method of claim 13, wherein the second substrate is flexible.

* * * * *